United States Patent [19]

Law et al.

[11] 4,261,915
[45] Apr. 14, 1981

[54] SILOXANE-TIN COATINGS

[75] Inventors: Gabriel H. Law, Whittier; Albert P. Gysegem, Monrovia, both of Calif.

[73] Assignee: Ameron, Inc., Monterey Park, Calif.

[21] Appl. No.: 122,198

[22] Filed: Feb. 19, 1980

Related U.S. Application Data

[62] Division of Ser. No. 858,708, Dec. 8, 1977, which is a division of Ser. No. 718,149, Aug. 26, 1976, Pat. No. 4,080,190.

[51] Int. Cl.³ .............................................. C07F 7/22
[52] U.S. Cl. ................................................... 260/429.7
[58] Field of Search ...................................... 260/429.7

[56] References Cited

U.S. PATENT DOCUMENTS

| | | | |
|---|---|---|---|
| 2,956,045 | 10/1960 | Merker | 424/184 X |
| 3,167,473 | 1/1965 | Leebrick | 424/288 |
| 3,307,793 | 3/1967 | Gibbons | 260/45.75 K |
| 3,384,648 | 5/1968 | Itoi | 260/429.7 |
| 3,392,036 | 7/1968 | McLeod | 106/287.16 |
| 3,541,215 | 11/1970 | DeMarco | 424/288 |
| 3,653,930 | 4/1972 | Law et al. | 106/1 |
| 3,917,648 | 11/1975 | McLeod | 260/37 SB |
| 3,927,052 | 12/1975 | Vizurraga | 260/429.7 |

FOREIGN PATENT DOCUMENTS 936408 9/1963 United Kingdom .

Primary Examiner—Paul F. Shaver
Attorney, Agent, or Firm—Christie, Parker & Hale

[57] ABSTRACT

Compositions for protecting materials from growth of pestiferous organisms, and particularly for protecting marine surfaces from fouling organisms, are formed from precursors having the formula

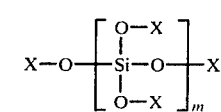

where m is from 1 to about 10, where each X is independently selected from the group consisting of alkyl and alkoxyalkyl radicals containing less than about 6 carbon atoms and Y, where Y has the formula

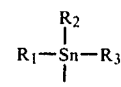

where $R_1$, $R_2$ and $R_3$ are independently selected from the group consisting of alkyl, cycloalkyl, and aryl radicals, where $R_1$, $R_2$ and $R_3$ contain in combination up to about 18 carbon atoms. The ratio of the tin atoms to silicon atoms in the precursors is at least about 1:50.

The precursors can be directly used as an additive for coatings. The precursors can also be used by subjecting them to hydrolysis and polycondensation to form an organotin substituted polysiloxane for use as an additive and a binder for coatings.

2 Claims, No Drawings

SILOXANE-TIN COATINGS

CROSS REFERENCE TO RELATED APPLICATIONS

This is a division of application Ser. No. 858,708, filed Dec. 8, 1977, which is a division of application Ser. No. 718,149, filed Aug. 26, 1976, now U.S. Pat. No. 4,080,190.

BACKGROUND OF THE INVENTION

This invention relates to methods and compositions for protecting materials from growth of pestiferous organisms, and particularly for preventing marine surfaces from fouling.

Organotin compounds such as trialkyl- and triarylorganotin compounds are used for control of fungi, bacteria, and marine organisms. However, their use has been limited because of certain deficiencies. For example, these compounds may be phytotoxic and possess a high mammalian toxicity. They may have a disagreeable odor and relatively high vapor pressure which limits their use in such areas as aerosol spray applications. These compounds also lack durability because they can be removed readily from a treated surface by rubbing, washing, and extraction. This is particularly true when they are used as additives in antifouling coatings for marine surfaces, where these compounds have been shown to be effective for only one to two years. This short effective life is attributed to leaching of the compounds from the coating matrix.

Leebrick in U.S. Pat. No. 3,167,473, describes biologically active polymers obtained by polymerizing a compound having the formula $R_3SnOCR'$ where R is an alkyl or phenyl radical and R' is a polymerizable organic group such as the vinyl radical. Although Leebrick's polymers are more durable than organotin compounds by themselves, these polymers have limited strength and durability and can exhibit incompatibility with inorganic zinc coatings, which are commonly used to provide corrosion resistance to marine surfaces.

Thus there is a need for biologically active materials for forming coatings to protect materials such as marine surfaces against the growth of pestiferous organisms where the coating has improved strength, longer antifouling service life, and is compatible with inorganic zinc coatings. An additional objective is to develop biological active compounds as additives to conventional paints to provide very low leaching of the toxicant and thus longer service life to the antifouling paint.

SUMMARY OF THE INVENTION

This invention is for precursors for forming compositions having the above features. The precursors have the formula

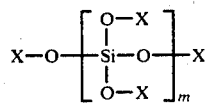

where m is from about 1 to about 10; where each X is independently selected from the group consisting of alkyl and alkoxyalkyl radicals containing less than about 6 carbon atoms and Y, where each Y in the precursor is independently a trisubstituted tin radical having the formula

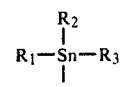

where $R_1$, $R_2$, and $R_3$ are independently selected from the group consisting of alkyl, cycloaklyl, and aryl radicals where $R_1$, $R_2$, and $R_3$ contain in combination up to about 18 carbon atoms. The X's are selected so that the ratio of tin atoms to silicon atoms in the precursors is at least about 1:50.

Preferably the Y's in the precursors are selected from the group consisting of tripropyl, tributyl, tricyclohexyl, and triphenyl tin radicals so compositions formed from the precursors have a broad spectrum of activity against pestiferous organisms. Preferably X's which are not Y are the ethyl radical.

When a precursor is used to form a binder for coating compositions it can be provided partially hydrolyzed, and preferably it is from about 70 to about 90% hydrolyzed.

To form a satisfactory binder from a precursor, X's are selected so that the ratio of tin atoms to silicon atoms in the precursor is from about 1:50 to about 2:5, and preferably from about 1:12 to about 1:3, and $R_1$, $R_2$, and $R_3$ are selected from the group consisting of alkyl and cycloalkyl radicals. If $R_1$, $R_2$, and $R_3$ are aryl radicals and/or the ratio of tin atoms to silicon atoms in the precursor is greater than about 2:5, then the precursor is not satisfactory for forming binders. The precursor may then be used as an additive in a composition useful for protecting materials from growth of pestiferous organisms.

A precursor can be prepared by combining a silicate having the formula

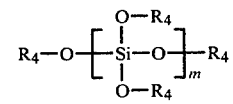

where $R_4$ represents the group consisting of alkyl and alkoxyalkyl radicals containing less than about 6 carbon atoms, and about n moles per mole of the silicate of a carboxylic acid derivative having the formula

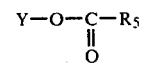

where the ratio of n to m equals the ratio of tin atoms to silicon atoms in the precursor, and where $R_5$ is selected from the group consisting of hydrogen and alkyl, cycloalkyl, and alkoxyalkyl radicals. The silicate and the carboxylic acid derivatives are reacted at a temperature below the temperature at which the precursor decomposes.

The precursor can also be formed by reacting a silicate having the formula

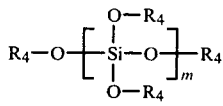

with about n/2 moles per mole of the silicate of water and about n/2 moles per mole of the silicate of a bis-trisubstituted tin oxide having the formula Y—O—Y, where each Y is independently a trisubstituted tin radical as above, and where the ratio of n to m equals the ratio of tin atoms to silicon atoms in the precursor. The silicate and tin oxide are reacted at a temperature below the temperature at which the precursor decomposes.

The precursor can also be formed by reacting a silicate having the formula

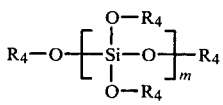

with about n moles per mole of the silicate of a trisubstituted tin hydroxide having the formula Y—OH, where Y is as defined above and the ratio of n:m equals the ratio of tin atoms to silicon atoms in the precursor. The silicate and tin hydroxide are reacted at a temperature below the temperature at which the precursor decomposes.

A biologically active cross-linked polysiloxane can be prepared from the precursor by hydrolysis of the precursor, preferably acid or base catalyzed, with polycondensation of the hydrolysis product. The polysiloxane formed consists essentially of the randomly cross-linked groups

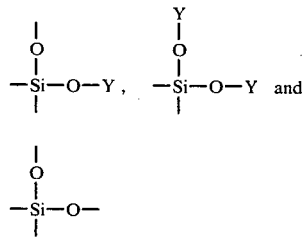

where each branch of the polysiloxane independently terminates with a structure selected from the group consisting of hydrogen and alkyl and alkoxyalkyl radicals containing less than about 6 carbon atoms and Y. Each Y in the polysiloxane is independently a trisubstituted tin radical as above.

When the cross-linked polysiloxane is used as a binder the polysiloxane comprises from about 5 to about 85% by weight of the total weight of the coating. To add corrosion resistance to the coating composition, selected anticorrosion components such as zinc oxide or metallic zinc can be included in the coating. When the cross-linked polysiloxane is used as an additive for forming an antifouling coating, the polysiloxane is comminuted and the coating comprises a paint base and from about 1 to about 70% by weight of the additive based on the weight of the coating.

The precursor can be provided as part of a system for preparing antifouling coatings for marine surfaces. In a system having two packages, a partially hydrolyzed binder is provided with a source of protons for effecting acid catalyzed hydrolysis, when the binder is exposed to moisture in the atmosphere, and a second package is provided which contains a filler for forming the coating. If the filler is nondeleteriously reactive with the source of protons, the filler can be combined with the precursor and source of protons in the same package.

Similarly, the precursor can be provided as a two-package system where the precursor is packaged with a hydroxyl source in the first package and a filler in the second package. If the filler is nondeleteriously reactive with the hydroxyl source, the filler can be supplied with the precursor and hydroxyl source together in the same package.

These and other features, aspects and advantages of the present invention will become more apparent with respect to the following description and appended claims.

DESCRIPTION OF THE INVENTION

Precursors for forming compositions for protecting materials from growth of pestiferous organisms have the formula

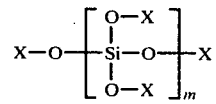

where m is from about 1 to about 10; where each X is independently selected from the group consisting of alkyl and alkoxyalkyl radicals containing less than about 6 carbon atoms and Y; where each Y in the precursor independently is a trisubstituted tin radical having the formula

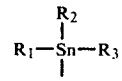

where $R_1$, $R_2$, and $R_3$ are independently selected from the group consisting of alkyl, cycloalkyl, and aryl radicals, where $R_1$, $R_2$, and $R_3$ contain in combination up to about 18 carbon atoms, and where the X's are selected so that the ratio of tin atoms to silicon atoms in the precursor is at least about 1:50. All the X's can be Y to give a tin atom to silicon atom ratio of (2m+2):m. The Y's in the precursor can be the same or different.

These precursors can be used for forming biologically active coatings, and for preparing additives for use in biologically active coatings. As used herein, the term "biologically active" as applied to a composition means the composition prevents growth of pestiferous organisms. These coatings may be used for treating materials to protect them from growth of pestiferous organisms. Illustrative of these materials are fibrous materials such as textiles and wood; plastics, including foam plastics; paint, varnishes and adhesives; seeds, plants, and tubers; and leather. It is particularly advantageous to treat materials which are not themselves subject to attack by organisms, but upon which organisms may grow, such as marine surfaces. These include concrete and metallic surfaces exposed to sea water, and metal or vitreous surfaces containing process waters, etc. Treatment of a material with a biologically active coating prepared from these precursors produces a surface resistant to attack by a broad spectrum of pestiferous organisms. These organisms can include fungi, bacteria, mold, slimes, mildew, and marine organisms such as algae, barnacles, limnora, toredo, tube worms, hydroids, and bryozoans.

In the above formula for the precursors, preferably m is less than about 10 so the precursor can be polymerized by hydrolysis and polycondensation. Depending upon the ratio of tin atoms to silicon atoms in the precursor and the nature of X, the precursor can even be a waxy solid at room temperature.

In a mixture of precursor molecules, m represents the average number of silicon atoms per precursor molecule. Generally there is a random distribution of molecules comprising more and less than m silicon atoms. For example, where m equals 5, precursor molecules containing 4, 5 and 6 silicon atoms are present.

X is limited to alkyl and alkoxyalkyl radicals containing less than about 6 carbon atoms so that the alcohol analog of X formed during hydrolysis of the precursor has sufficient volatility to evaporate so the precursor can cure. Generally, the higher the molecular weight of X, the lower the volatility of its alcohol analog. Exemplary of the radicals which X can be are methyl, ethyl, n-propyl, isopropyl, n-butyl, isobutyl, methyloxymethyl, methyloxyethyl, and the like. Preferably, X is the methyloxyethyl or ethyloxyethyl radical when low volatility is required under certain conditions such as coating interior surfaces or under high temperature operating conditions.

$R_1$, $R_2$, and $R_3$ can be lower alkyl radicals containing less than about 10 carbon atoms such as ethyl, propyl, isopropyl, n-butyl, sec-butyl, tert-butyl, amyl, hexyl, octyl, nonyl, isooctyl radicals, and the like. R can also be a substituted lower alkyl radical. Substituents include chloride, bromide, ether and aryl substituents, and the like.

$R_1$, $R_2$ and $R_3$ can be a lower cycloalkyl radical such as the cyclohexyl radical and substituted lower cycloalkyl radicals.

$R_1$, $R_2$, and $R_3$ can be an aryl radical such as the phenyl radical and substituted phenyl radicals. Substituents include chloride, bromide, ether, and alkyl substituents, and the like. Thus $R_1$, $R_2$, and $R_3$ can be chlorophenyl, bromophenyl, nitrophenyl, tolyl, xylyl, ethylphenyl, and the like. When $R_1$, $R_2$, and $R_3$ are all aryl radicals and the precursor has a tin to silicon atom ratio of about 1:5, the precursor is a solid with only slight solubility in common solvents. Thus if the precursor is to be used for forming a binder for coating compositions, $R_1$, $R_2$, and $R_3$ generally cannot all be aryl radicals.

Preferably, $R_1$, $R_2$, and $R_3$ are the same because trisubstituted tin compounds where the tin is substituted with the same radical are commercially available. However, $R_1$, $R_2$, and $R_3$ can be different such as where Y is the octyl-dimethyl tin radical.

The total number of carbon atoms comprising a trisubstituted tin moiety has a large effect on its biological activity. The effect appears to be one of size rather than chemical or electronic effect. For example, the octo-yldimethyl and the tributyl tin radicals, which have about the same number of carbon atoms, exhibit about the same toxicity toward mammals and fouling organisms. In general, small moieties, such as the trimethyl tin and triethyl tin radicals, show only slight toxicity toward bacteria and marine fouling organisms, but extremely high toxicity toward mammals, including man. Tripropyl tin and tributyl tin, on the other hand, exhibit low toxicity toward man, but are the most effective trialkyl tin compounds for antifouling use. As the total number of carbons in a trialkyl tin compound increases above about 12 to 14, both the human toxicity and antifouling activity decrease due to the increase of the total number of carbon atoms.

Preferably, when $R_1$, $R_2$, and $R_3$ are alkyl radicals, the total number of carbon atoms in $R_1$, $R_2$, and $R_3$ in combination is less than about 14 carbon atoms for high biological activity. Generally, $R_1$, $R_2$, and $R_3$ contain less than about 18 carbon atoms in combination so that compositions effective in protecting materials from growth of pestiferous organisms can be prepared from a precursor.

Preferably, $R_1$, $R_2$, and $R_3$ are selected so that Y is the tributyl, tripropyl, triphenyl or tricyclohexyl tin radical. These radicals are preferred because they are broad-spectrum toxicants, especially for many marine organisms, and display minimal toxicity to man.

A precursor preferably has a ratio of tin to silicon atoms greater than about 1:50 because at ratios less than about 1:50 a coating prepared with the precursor has inadequate biological activity to be of much commercial value. The maximum ratio of tin to silicon atoms in the precursor occurs when all the X's are Y's. This gives a ratio of tin to silicon atoms of $(2m+2):m$.

The optimum tin to silicon atom ratio of a precursor used for forming a binder is a balance of competing considerations. On one hand, the higher the tin to silicon atom ratio, the more effective and more long-lived is a coating formed from the precursor. However, at higher ratios of tin to silicon atoms, curing of the precursor by hydrolysis and polycondensation to form a polysiloxane becomes progressively more difficult. At tin to silicon atom ratios greater than about 2:5, the precursor is not suitable for preparing binders for coating compositions because the precursor remains soft and does not cure to sufficient hardness to be used as a coating. It is believed that a precursor having a tin to silicon atom ratio greater than about 2:5 is unsatisfactory for forming binders because the bulky organotin group prevents polymerization by either blocking the attack of water on the reactive sites of the precursor, or by inhibiting condensation of the intermediate silanol formed during hydrolysis with another silanol group.

A precursor for forming a biologically active polysiloxane binder preferably has a tin to silicon atom ratio of from about 1:12 to about 1:3. In this range it has been found that a hard, clear, solvent-resistant film exhibiting effective and long-lived biological activity in preventing fouling on marine surfaces can be formed with the precursor.

The precursor of this invention may be prepared by reacting a silicate having the formula

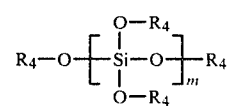

with about n moles per mole of the silicate of a carboxylic acid derivative having the formula

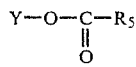

where m and Y are as above, and where the ratio of n to m is at least about 1:50 to give a desired tin to silicon atom ratio as described above. $R_4$ represents the group consisting of alkyl and alkoxyalkyl radicals containing less than about 6 carbon atoms, i.e., $R_4$ is the organic portion of the group from which X is selected. Each $R_4$ may be the same or different.

$R_3$ is selected from the group consisting of hydrogen, and alkyl, cycloalkyl, and alkoxyalkyl radicals. $R_5$ is selected for convenience, i.e., so that the carboxylic acid ester found in the reaction is sufficiently volatile to be removed easily from the product.

The silicate and carboxylic acid derivative react to form a precursor according to the equation

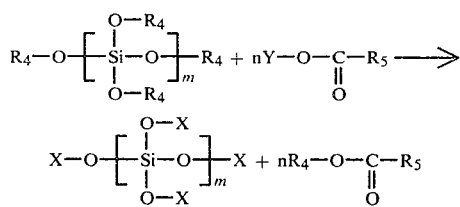

where each X is as defined above. Exemplary of silicates and carboxylic acid derivatives which can be used are "Ethyl Silicate 40" and tributyltin acetate. "Ethyl Silicate 40" is the trade name for an ethyl polysilicate available from Union Carbide Chemical Company. This material is a light-colored liquid having an $SiO_2$ content of about 40% and comprising polysilicates having an average of 5 silicon atoms per molecule, i.e., m equals 5, although individual molecules can comprise only 1 silicon atom. "Ethyl Silicate 40" and tributyltin acetate react according to the equation

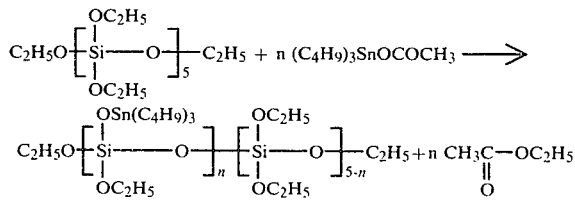

The tributyltin substituted silicon atoms are randomly located along the chain, and a single silicon atom can be substituted by none, one, two or three tributyltin groups, or for a molecule having only 1 silicon atom, four tributyltin groups.

The reaction of the silicate and the carboxylic acid derivative is conducted at an elevated temperature, and at least at a temperature sufficiently high that the carboxylic acid derivative melts. The silicate and carboxylic acid derivative are reacted at a temperature below the temperature at which the precursor prepared from the silicate and carboxylic acid derivative decomposes. Decomposition may be evidenced by darkening of the precursor and a hydrocarbon-like odor. For example, when preparing a precursor from tributyltin acetate and Ethyl Silicate 40, the temperature should be maintained from about 160° to about 180° C.

Another method for preparing the precursor of this invention is to combine a silicate, as described above, with about n/2 moles per mole of the silicate of water and n/2 moles per mole of the silicate of a bistrisubstituted tin oxide having the formula Y—O—Y where Y and n have the same meaning as above. Generally, a silicate reacts at a lower temperature with a tin oxide than with the carboxylic acid derivative of the tin oxide. For example, bis-tributyltin oxide reacts at a fast rate with Ethyl Silicate 40 in the presence of water at about 85° C. compared to the 160° C. required when tributyltin acetate is used. The silicate and tin oxide are combined at a temperature below the temperature at which the precursor formed from the tin oxide and the silicate decomposes.

Another method for preparing the precursors of this invention is to combine a silicate as described above with about n moles per mole of the silicate of a trisubstituted tin hydroxide having the formula Y—OH, where Y and n have the same meaning above. The silicate and tin hydroxide are combined at a temperature below the temperature at which the precursor formed from the tin hydroxide and the silicate decomposes.

A solvent can be used in which the reactants used for preparing the precursor are soluble. The appropriate solvent depends upon the nature of the silicate and the tin oxide, tin hydroxide or carboxylic acid derivative used. Suitable solvents for alkyl silicates include acetone, diacetone, alcohol, isopropanol, pentanone, and various blends thereof.

The precursors can be used for forming compositions for protecting materials from growth of pestiferous organisms either with or without polymerizing the precursor. Without polymerization, a precursor can be used as a biologically active additive to form a biologically active composition, and with polymerization to form an organotin substituted, cross-linked polysiloxane. This polysiloxane can be used as a binder for a biologically active coating composition or can be comminuted to small particles to serve as an additive for biologically active compositions. The polysiloxane can be comminuted by any physical act of size reduction, including, but not limited to chopping, crushing and grinding by suitable machinery.

Particulate cross-linked polysiloxane can also be obtained by forming droplets of at least partially hydrolyzed precursor and then exposing the droplets to a source of moisture at a temperature sufficient to result in condensation of the precursor. Ambient temperature can be satisfactory to effect condensation. Each of the droplets thereby forms a cross-linked polysiloxane particle useful as an additive in a biologically active composition. Droplets can be formed by spraying the precursor with conventional spray equipment. Preferably the precursor is hydrolyzed as much as possible before it is sprayed to ensure that the droplets solidify before the droplets can contact a structure or self-coalesce. This can be effected advantageously by spraying the precursor with steam by means such as a venturi nozzle. To ensure that adequate moisture is available for complete hydrolysis of the precursor, the droplets can be sprayed into a humid atmosphere. The hydrolysis and condensation of the droplets can be catalyzed with a proton or hydroxyl source as described below. The advantage of preparing particulate polysiloxane using this method of polymerizing small droplets of the precursor is that the operating and capital costs associated with a comminution step are eliminated.

When a precursor or comminuted polysiloxane is used as an additive in a biologically active coating composition, the composition can also contain nonbiologically active diluents which can serve as a carrier. The diluent can be a solvent such as benzene, toluene, naphtha, mineral spirits, ligroin, acetone, diacetone, alcohol, or various blends thereof. The diluent may be a liquid dispersant which is not a solvent for the precursor or polysiloxane such as water. Suitable solid diluents include talc, limestone, diatomaceous earth and the like. Other diluents include oil-based and water-based paints and organic polymeric coatings such as acrylic, polyethylene, polypropylene, polystyrene, polyurethane, and polyvinyl chloride coatings.

Where the precursor or the comminuted cross-linked polysiloxane is employed as a biologically active additive in a biologically active composition, the precursor or polysiloxane typically comprises from about 0.01% to about 80% by weight of the composition.

As used herein, the term "biologically active additive" refers to a precursor, as described above, used as an additive and a cross-linked polysiloxane formed from such a precursor, when the cross-linked polysiloxane is used as an additive. It does not include a biologically active polysiloxane used as a binder for a coating.

The particular composition employed and the amount of biologically active additive contained therein is chosen in accordance with the material treated and the pestiferous organism against which protection is desired. For example, when a biologically active additive is employed as an active ingredient of an antifouling coating composition, the additive is employed in the amount of from about 1 to about 70% by weight of the total composition. When the biologically active additive is present in the antifouling coating at a level less than 1%, inadequate protection from fouling organisms results. The higher the concentration of the biologically active additive, the more effective the composition in preventing fouling. However, at compositions greater than about 70% by weight based on a total weight of the coating, the coating has poor physical properties.

Antifouling coating compositions containing a biologically active additive can also contain a paint base such as vinyl, acrylic, and alkyd resin bases. They can also contain a pigment such as titanium dioxide, a thickener such as bentonite, fillers such as aluminum silicate and calcium silicate, and driers such as cobalt naphthenate and manganese naphthenate. They may also contain solvents or thinners such as mineral spirits, naphtha, benzene, toluene, methylethyl ketone, and the like.

Antifouling coatings for marine surfaces can be prepared with a biologically active cross-linked polysiloxane binder formed from the above described precursors. One type of useful coating contains a filler in addition to the biologically active binder. As the ratio of binder to filler in a coating composition increases, the coating's strength and biological activity increase, but its adhesion to marine surfaces decreases. The coating comprises preferably at least about 5% by weight of the biologically active polysiloxane binder so the coating has sufficient strength and biological activity to protect marine surfaces from fouling, and preferably less than about 85% by weight of the binder so the coating has adequate adhesion to marine surfaces to prevent sloughing off in use.

The binder to filler ratio in the coating depends upon the density of the filler. For example, with a light filler such as china clay or titanium dioxide, the coating preferably contains from about 10 to about 85% binder. For a dense filler such as zinc dust, the coating contains from only about 5% up to about 50% binder. More preferably, a coating containing zinc as a filler comprises from about 20 to about 40% by weight binder based on the total weight of the coating so the coating is strong, durable, adherent, biologically active, and has anticorrosion properties.

Conventional fillers can be used in coatings containing biologically active polysiloxane binders. These include silica powder, talc (magnesium silicate), china clay (aluminum silicate), Wollastonite (calcium silicate), barytes (barium sulfate), barium metaborate, and the like. Pigments such as iron oxide, chrome yellow, and chrome green may also be used. Organic dyes may also be used to color the product. Zinc oxide can be used to aid film hardening and resistance to growth of algae. Anticorrosion-antifouling coatings useful for direct application over a clean steel surface can be prepared by using a biologically active polysiloxane binder and a metallic filler such as zinc. Copper and cuprous oxide can be used as fillers to enhance the antifouling properties of a coating.

The biologically active cross-linked polysiloxanes prepared from the precursors of this invention consist essentially of the randomly cross-linked groups

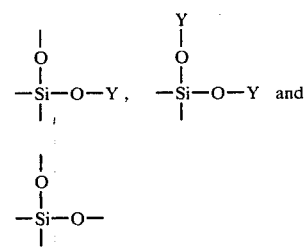

where each branch of the polysiloxane independently terminates with a structure selected from group consisting of alkyl and alkoxyalkyl radicals containing less than about 6 carbon atoms and Y. Each Y is independently a trisubstituted tin radical as defined above. Each Y in the polysiloxane can be the same or different.

The cross-linked polysiloxane is prepared from the precursor by hydrolysis followed by polycondensation. The hydrolysis of alkylsilicates at a neutral pH is generally too slow to be able to use the silicate as a binder in coating formulations. However, in either acidic or basic medium, the rate of hydrolysis is appreciably increased. In acid conditions, achieved by adding small amounts of an acid to the water used in the hydrolysis, the equilibrium conditions are reached in hours. These equilibrium conditions, which are,

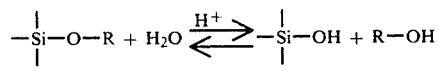

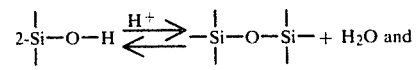

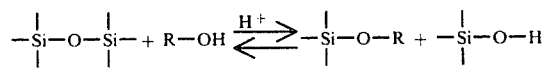

all occur simultaneously. Also under acid conditions, the tendency for linear chain extension is much stronger than for cross-linking. All of these account for the liquid nature of the partially hydrolyzed precursor when in a closed system where no alcohol can escape and no additional water is added. In the atmosphere, the alcohol can evaporate, thereby driving the equilibrium toward the condensed silicate form. Additional water from atmospheric moisture or from immersion in either fresh or sea water completes the hydrolysis. The end product is a thoroughly cross-linked structure of Si—O—Si bonds. This structure is terminated inside and outside with Si—OH groups. In the organotin polysiloxanes of this invention a Si—O—Y group eventually becomes hydrolyzed itself, though this is a much slower process than the hydrolysis of the Si—O—R group in the precursor to form the cross-linked polysiloxane. Hydrolysis of Si—O—Y in the cross-linked polysiloxane yields

and an organotin compound slightly soluble in water, such as YOH, $Y_2O$, $YHCO_3$, or $Y_2CO_3$. It is believed that recombination of the organotin compound with some

can occur. This may account in part for the low leaching rates which have been experienced for the leaching of tin from the organotin substituted polysiloxane coatings of this invention.

Dilute aqueous hydrochloric acid can be used to catalyze the hydrolysis and condensation of the precursor. Other acids which can be used as catalysts include mineral acids such as sulfuric acid, orthophosphoric acid, and nitric acid, and organic acids such as trichloracetic acid, formic acid and oxalic acid. The amounts to be used vary for each acid, but the optimum quantity can readily be determined by a chemist of ordinary skill in the art. The action of organic acids generally is slower than that of inorganic acids. Therefore, a binder catalyzed with an organic acid preferably is immersed in or sprayed with water after the binder has set to help the coating attain its final hardness.

A solvent for the precursor may be used to aid in acid catalyzed hydrolysis. Preferably a volatile solvent is used so that quick drying of a coating formed from the precursor occurs. Exemplary of solvents which can be used are acetone, isopropanol, pentanone, and methylisobutyl ketone, which is preferred because it seems to stabilize the hydrolyzed precursor.

Hydrolysis of the precursor can also be catalyzed by a hydroxyl source which itself is nonreactive with the precursor but which reacts with moisture to produce hydroxyl ions, such as described in U.S. Pat. No. 3,653,930, issued to Law et al, assigned to the assignee of this invention, and incorporated herein by reference. This patent describes catalyzing hydrolysis of silicates with a hydroxyl source nonreactive with the silicate and reactive with moisture to produce hydroxyl ions. Exemplary of hydroxyl sources disclosed in U.S. Pat. No. 3,653,930 are organic sources such as amines such as mono-, di- and triethanolamine, diamylamine, cyclohexylamine, piperidine, and the like, and inorganic hydroxyl sources such as potassium, sodium and lithium hydroxide.

A solvent may also be used when the precursor is hydrolyzed with the aid of a hydroxyl source. Exemplary of the solvents which can be used are those listed in Table I of U.S. Pat. No. 3,653,930.

The precursors of this invention can be supplied for preparing biologically active coating compositions in a two-package system where a first package contains the precursor, a solvent, and acid water or a hydroxyl source, and a second package contains filler. When the filler does not deleteriously react with the proton or hydroxyl source, a one-package system can be used. For example, if the filler contains zinc and an acid is used to catalyze the hydrolysis, a one-package system cannot be used because the zinc reacts with the acid with resultant gelation of the precursor. However, if the filler contains zinc and an amine is used for catalyzing the hydrolysis, then a one-package system may be used.

The precursor should be provided in a moisture-proof type container so that hydrolysis and condensation do not occur prematurely.

The precursor can be supplied partially hydrolyzed when acid catalyzed hydrolysis is used to reduce the cure time of the precursor to form a biologically active polysiloxane binder. Solvent can be added to the package containing the precursor to reduce the viscosity of the coating composition for easier application to the surface to be protected.

In base catalyzed hydrolysis of the precursors, water is not provided in the same container used for the precursor and hydroxyl source. This is because the rate of hydrolysis of a precursor catalyzed by a hydroxyl source is much faster than acid catalyzed hydrolysis, and when a hydroxyl source is used, cross-linking of the precursor appears to be as favored as linear chain extension. Thus even small amounts of water in the same container as the precursor and hydroxyl source can cause gelatin.

Ability to prepare a strong, durable coating from the precursor depends upon the degree of hydrolysis of the precursor. Generally, as the degree of hydrolysis of the precursor used to prepare a coating increases, adhesion of the coating to the material to be protected worsens, cure time of the coating shortens, shelf-life of the precursor shortens, and viscosity of the precursor increases. In preparing a system, all these factors are balanced in choosing the degree of hydrolysis of the precursor. It is generally preferred that the precursor be hydrolyzed to at least about 50%, and more preferably from about 70 to 90%, to obtain a coating system which has good adhesion to most marine surfaces, cures quickly, has a shelf-life of at least six months and has sufficiently high viscosity that it can be applied to vertical surfaces.

Degree of hydrolysis of the precursor is determined by the ratio of the number of moles of water used to hydrolyze the precursor to the number of moles of water required for complete hydrolysis. Complete hydrolysis requires one mole of water per two moles of alkyl and alkoxyalkyl groups comprising the precursor.

If the silicon atoms are completely substituted with trisubstituted tin radicals, the precursor cannot be polymerized to form a cross-linked polysiloxane.

The suitability of a system for forming coatings also depends upon the solvent used and the amount of solvent present. Generally, increasing the amount of solvent present lengthens cure time, lengthens shelf-life, and decreases the viscosity of the precursor/solvent mixture.

Coating compositions prepared from the precursor can be applied to a surface to be treated by conventional techniques such as spraying or brushing. Curing occurs by absorption of atmospheric moisture at ambient temperatures. However, if desired, the applied coating can be heated and/or exposed to a source of moisture for quick curing. When used as an antifouling agent, the coatings can be applied to new construction, over inorganic primers, and over inorganic coatings containing anticorrosion agents such as metallic zinc.

The biological activity of compositions prepared according to this invention is due to leaching of trisubstituted tin radicals from the composition. It is believed that leaching occurs due to slow hydrolysis of the biologically active additive or cross-linked polysiloxane binder, where the bond between an oxygen and tin atom is hydrolyzed.

These and other features of the present invention will become better understood with reference to the following examples.

EXAMPLE 1 (Preparing a Precursor)

To a 1,000 ml. round bottom flask equipped with a magnetic stirrer, heating mantle, pot thermometer, and distilling condenser, 298.1 g. (0.4 moles) of Ethyl Silicate 40 and 181.3 g. (0.52 moles) tributyltin acetate were added. The contents of the flask were slowly heated until the tributyltin acetate melted and dissolved in the Ethyl Silicate 40. The mixture was then heated to 160° C. with continuous stirring. At 140° C. the reaction was sufficiently rapid that boiling began with generation of ethyl acetate. The mixture was maintained at about 160° C. until about 90% of the expected amount of ethyl acetate was recovered. The reaction was then stopped by removing the heating mantle. At room temperature the precursor formed was a yellow liquid.

EXAMPLE 2 (Preparing a Precursor)

Using the equipment used with Example 1, 59.5 g. (0.1 mole) of bis-tributyltin oxide and 1.8 g. (0.1 mole) of water were heated to 85° C. Then 149.0 g. (0.2 mole) of Ethyl Silicate 40 were added while maintaining the reactants at 85° C. Ethanol released by the reaction was collected. The reaction was stopped by removing the heating mantle when about 90 to 95% of the calculated amount of ethanol to be produced was collected. The reaction proceeded at a lower temperature than the reaction of Example 1, i.e., 85° C. compared to 160° C. The precursor formed was a pale yellow liquid at room temperature.

EXAMPLE 3 (Preparing a Precursor)

Using the method and equipment of Example 1, 372.6 g. (0.5 moles) of Ethyl Silicate 40 and 174.4 g. (0.5 moles) of tributyltin acetate were reacted to form a yellow liquid.

EXAMPLE 4 (Preparing a Precursor)

Using the equipment of Example 1, 366.7 g. (1 mole) triphenyltin acetate and 209 g. (1 mole) tetraethyl orthosilicate were mixed together. The mixture was heated until reaction began at about 75° to 80° C. with distillation of ethyl acetate. The reaction was continued until 80 ml of ethyl acetate was collected. The distillate smelled of benzene, indicating some decomposition had occurred. When cooled, the product was a hard, waxy, white solid.

EXAMPLE 5 (Preparing a Precursor)

In a 500 ml. reaction flask equipped with a magnetic stirrer, distillation head, condenser pot, thermometer, and heating mantle, 96.2 g. (0.25 mole) of tricyclohexyltin hydroxide and 186.3 g. (0.25 mole) of Ethyl Silicate 40 were slowly heated. The solid tricyclohexyltin hydroxide melted and dissolved in the Ethyl Silicate 40 at about 70° C. The reaction began shortly thereafter. The reaction was vigorous at 95° C. with distillation of ethanol, which was collected. The maximum reaction temperature was 135° C. The heating mantle was removed when 14 ml. of ethanol had been collected. At room temperature the precursor formed was a cloudy, slightly yellow liquid.

EXAMPLE 6 (Preparing a Precursor)

To a 250 ml. flask equipped with a magnetic stirrer, heating mantle, thermometer, distillation head, and condenser, 69.7 g. (0.2 moles) of tributyltin acetate and 41.8 g. (0.2 moles) of tetraethyl orthosilicate were added. The contents of the flask were slowly heated until the tributyltin acetate melted and dissolved in the tetraethyl orthosilicate. The reaction began at about 165° C. as evidenced by boiling. The mixture was maintained at about 165° C. until about 17.5 ml. of ethyl acetate (90% of theoretical yield) were collected. The product was a clear, slightly yellow liquid.

EXAMPLE 7 (Preparing a Precursor)

Using the method and apparatus of Example 6, 87.2 g. (0.25 moles) of tributyltin acetate and 26.1 g. (0.125 moles) of tetraethyl orthosilicate were reacted to produce a clear, slightly yellow liquid.

EXAMPLE 8 (Preparing a Polysiloxane)

300 g. of the precursor prepared in Example 3 were combined with 170.4 g. of isopropyl alcohol. To achieve a theoretical 100% hydrolysis; 26.6 g. of 1% aqueous sulfuric acid were then slowly added to the precursor/alcohol solution. The resultant polysiloxane was placed in an open beaker in an oven at 50° C. until thoroughly solidified. The solidified material was crumbled and returned to the oven to dry over night.

EXAMPLE 9 (Preparing a Polysiloxane Film)

Three hundred grams of the precursor of Example 1 were combined with 173.4 grams of isopropyl alcohol. To achieve a theoretical 100% hydrolysis, 26.6 grams of a 1% aqueous solution of sulfuric acid were added to the precursor/alcohol solution, a few drops at a time, allowing the solution to become clear after each addition. It was noted that when the alcohol solvent was not used, high local concentrations of water resulted in precipitation of solid material. A portion of the solution was then placed in an air-tight container at room temperature to determine shelf-life and another portion was placed in a 50° C. oven for 18 hours to complete hydrolysis. The hydrolyzed solution was spread on glass at room temperature and allowed to condense to form a film. The shelf-life at room temperature of the hydrolyzed precursor and properties of the film produced are summarized in Table 1.

EXAMPLES 10–16 (Polysiloxane Films)

Using the methods of Examples 1 and 10, a 100% hydrolyzed precursor was prepared from tributyltin acetate (TBTA) and Ethyl Silicate 40 (ES-40) in mole ratios ranging from 0.1:1 to 2.5:1 as presented in Table 1. The mole ratio of tin to silicon in the hydrolyzed precursor is equal to 1/5th of the mole ratio of TBTA to ES-40 used to prepare the precursor.

As shown in Table 1, as the level of tributyltin in the precursor increased, its shelf-life increased and the resistance to film cracking of a film formed from the precursor increased. At a mole ratio of TBTA to ES-40 of 0.1:1, the film formed had inadequate adhesion and flaked off. At mole ratios from about 0.4:1 to about 1.3:1, the film formed had good hardness, but at mole ratios of TBTA to ES-40 higher than about 1.7:1, the film hardness became poor.

TABLE 1

| Example No. | Binder | Mole Ratio | Film Hardness | Film Cracking | Shelf Life |
|---|---|---|---|---|---|
| 10 | A | 0.1/1 | flake-off | severe | gelled after 1 mo. |
| 11 | B | 0.4/1 | good | moderate | gelled after 1 mo. |
| 12 | C | 0.7/1 | good | slight | gelled after 2 mo. |
| 9 | D | 1.0/1 | good | minor | gelled after 2 mo. |
| 13 | E | 1.3/1 | good | none | gelled after 6 mo. |
| 14 | F | 1.7/1 | fair | none | ok after 1 yr. |
| 15 | G | 2.0/1 | poor | none | ok after 1 yr. |
| 16 | H | 2.5/1 | poor | none | ok after 1 yr. |

EXAMPLE 17 (Antifouling Coating)

An antifouling coating is prepared by pulverizing a portion of the dried polysiloxane prepared in Example 8 in a high-speed laboratory blender. Thirty parts by weight of the pulverized polysiloxane are combined with a 100 parts by weight of a vinyl coating, the composition of which is presented in Table 2.

TABLE 2

| | % by Wt. |
|---|---|
| Vinyl resin copolymer (by Union Carbide) VMCH | 10 |
| VYHH | 3 |
| Pigments: Titanium dioxide | 7 |
| Lamp black | 1 |
| Magnesium silicate extender | 5 |
| Plasticizer (Chlorowax 40 by Diamond Shamrock) | 14 |
| Toluene solvent | 30 |
| Methylethyl ketone solvent | 30 |
| | 100 |

EXAMPLE 18 (Antifouling Coating)

An antifouling coating is prepared by combining polysiloxane of Example 8 with an equal weight of 2-methoxy ethanol in a ball-mill until a paste of fine dispersion is obtained. Sixty parts by weight of the dispersion are combined with 100 parts by weight of the vinyl coating of Table 2.

TABLE 3

| | % by Wt. |
|---|---|
| Chlorinated rubber resin (Parlon 10 by Hercules Chemical Co.) | 11 |
| Chlorinated Paraffin (Chlorowax 40 by Diamond Shamrock) | 9 |
| Plasticizer: Dioctyl Phthalate | 2.5 |
| Organometallic Heat Stabilizer (Thermolite 31 M & T Chemicals) | .5 |
| Pigment: Red iron oxide | 5.0 |
| Filler: Silica filler | 20.00 |
| Solvent: Xylene | 52.00 |
| | 100.00 |

EXAMPLE 19 (Antifouling Coating)

An antifouling chlorinated rubber coating is prepared by combining 30 parts by weight of the biologically active polysilocane additive of Example 17 with 100 parts by weight of the chlorinated rubber coating, the ingredients of which are presented in Table 3.

EXAMPLE 20 (Antifouling Coating)

Another chlorinated rubber antifouling coating is preapred by combining 60 parts by weight of the biologically active polysiloxane dispersion of Example 18 with 100 parts by weight of the chlorinated rubber coating of Example 19. The resultant coating is a satisfactory antifouling coating.

EXAMPLE 21 (Antifouling Coating)

An antifouling epoxy paint is prepared by combining the ingredients listed in Table 4 until a uniform dispersion is obtained. The resultant paint is applied by spraying or brushing concrete, wood, aluminum and steel substrates to provide protection from fouling.

TABLE 4

| | Parts by Weight |
|---|---|
| Epoxy resin (Epon 828 by Shell Chemical) | 18 |
| Aluminum silicate extender | 12 |
| Red iron oxide pigment | 3 |
| Xylene solvent | 30 |
| Polyamide curing agent (Versamid 140 by General Mills) | 13 |
| Precursor of Example 1 | 24 |

EXAMPLE 22 (Filler)

A filler for forming white antifouling coatings was prepared by mixing 56 parts by weight silica powder (100–200 mesh) with 33 parts by weight barium metaborate and 11 parts by weight zinc oxide. The filler was found to be satisfactory when used in antifouling topcoats for inorganic zinc primers.

EXAMPLE 23 (Filler)

A filler for forming red antifouling coatings was prepared by mixing 85 parts by weight silica powder (100–200 mesh) with 5 parts by weight rod iron oxide and 10 parts by weight zinc oxide. The filler was found to be satisfactory when used in antifouling topcoats for inorganic zinc primers.

EXAMPLE 24 (Filler)

A filler for forming green antifouling coatings was prepared by mixing 85 parts by weight silica powder (100–200 mesh) with 5 parts by weight chromic oxide and 10 parts by weight zinc oxide. The filler was found to be satisfactory when used in antifouling topcoats for inorganic zinc primers.

EXAMPLE 25 (Filler)

A filler for forming anticorrosion-antifouling coatings was prepared by mixing 98 parts by weight zinc dust having an average diameter of 8 microns and 2 parts by weight red iron oxide. The filler was found to be satisfactory for forming anticorrosion-antifouling coatings for direct application over sandblasted steel surfaces.

EXAMPLE 26 (Filler)

A filler for preparing anticorrosion-antifouling coatings was made by mixing 88 parts by weight zinc dust having an average diameter of 8 microns with 10 parts by weight silica powder (100–200 mesh) and 2 parts by weight red iron oxide. The filler was found to be satisfactory for forming anticorrosion-antifouling coatings for direct application over sandblasted steel surfaces.

EXAMPLES 27-35 (Antifouling Topcoats)

Antifouling coating compositions were prepared by 80% hydrolyzing the binders A-H of Table 1 and mixing 35 parts by weight of the hydrolyzed binder with 65 parts by weight of the filler of Example 22, for Examples 27–34 respectively. A control coating was prepared as Example 35 by mixing 35 parts by weight of 80% hydrolyzed unsubstituted Ethyl Silicate 40 with 65 parts by weight of the filler of Example 22. Sandblasted panels were first coated with an inorganic zinc primer and subsequently topcoated with a material from Examples 27 to 34, which cured to form antifouling topcoat in 3 to 4 minutes. Example 35 was a control. The coated panels were immersed in sea water in Florida for 12 months and visually inspected every two months for barnacle growth. The panels were rated for barnacle growth with a score of 0 meaning complete failure, i.e., the panel was coated with barnacles, and a score of 10 representing no barnacle growth. The results at 2, 4, 6 and 12 months are presented in Table 5. As shown in Table 5, as the ratio of tin to silicon atoms in the coating increased, improved resistance to barnacle growth occurred, with a ratio of tin to silicon atoms as low as 0.7 to 5 (Binder C) preventing barnacle growth for at least 1 year. On the other hand, the control, which contained no tributyltin, was almost a complete failure in as little as 2 months.

Leach rate of tin from the coating of Example 20 was determined before and after one year immersion in sea water in Florida. It was found that 0.4 microgram of tin per $cm^2$ of surface per day was leached from the coating, believed due to hydrolysis of the oxygen to tin bond. All topcoats have shown good compatibility with inorganic zinc primers.

TABLE 5

| | | Barnacle Growth | | | |
| | | Exposure Time (months) | | | |
| Example | Binder | 2 | 4 | 6 | 12 |
| --- | --- | --- | --- | --- | --- |
| 27 | A | 6-7 | 6 | 6 | 0 |
| 28 | B | 10 | 10 | 8-9 | 5 |
| 29 | C | 10 | 10 | 10 | 10 |
| 30 | D | 10 | 10 | 10 | 10 |
| 31 | E | 10 | 10 | 10 | 10 |
| 32 | F | 10 | 10 | 10 | 10 |
| 33 | G | 10 | 10 | 10 | 10 |
| 34 | H | 10 | 10 | 10 | 10 |

TABLE 5-continued

| | | Barnacle Growth | | | |
| | | Exposure Time (months) | | | |
| Example | Binder | 2 | 4 | 6 | 12 |
| --- | --- | --- | --- | --- | --- |
| 35 | Control | 1 | 0-1 | 1 | 0 |

EXAMPLES 36-43 (Antifouling-Anticorrosion Coatings)

Antifouling-anticorrosion coating compositions were prepared by 80% hydrolyzing the binders A–G of Table 1 and mixing 35 parts by weight of the hydrolyzed binder with 65 parts by weight of the filler of Example 25 for Examples 36–42 respectively. A control coating was prepared as Example 43 by mixing 35 parts by weight of 80% hydrolyzed unsubstituted Ethyl Silicate 40 with 65 parts by weight of the filler of Example 25. Sandblasted steel panels were coated with the mixture, which cured to form an antifouling coating in about 3 to 4 minutes. The coated panels were immersed in sea water in Florida for 12 months and visually inspected every two months for barnacle growth with a score of 0 meaning complete failure, i.e., the panel was coated with barnacles, and a score of 10 representing no barnacle growth. Test results at 2, 4, 6, and 12 months are presented in Table 6. As shown in Table 6, as the ratio of tin to silicon atoms in the coating increased, improved resistance to barnacle growth resulted, with a ratio of tin to silicon atoms as low as 0.4 to 5 (Binder B) preventing barnacle growth for 1 year. On the other hand, the control, which contained no tributyltin, was a complete failure as an antifouling coating in only two months.

TABLE 6

| | | Barnacle Growth | | | |
| | | Exposure Time (months) | | | |
| Example | Binder | 2 | 4 | 6 | 12 |
| --- | --- | --- | --- | --- | --- |
| 36 | A | 7 | 7 | 7 | 10 |
| 37 | B | 10 | 10 | 10 | 10 |
| 38 | C | 10 | 10 | 10 | 10 |
| 39 | D | 10 | 10 | 10 | 10 |
| 40 | E | 10 | 10 | 10 | 10 |
| 41 | F | 10 | 10 | 10 | 10 |
| 42 | G | 10 | 10 | 10 | 10 |
| 43 | Control | 0 | 0 | 0 | 0 |

Examples 36 to 42 can also be applied over inorganic zinc primers for maximum corrosion protection and antifouling strength.

Thus, this invention provides high strength antifouling coatings compatible with inorganic zinc coatings and having long term effectiveness against growth of fouling organisms.

What is claimed is:

1. A method of preparing particles of a polysiloxane consisting essentially of the randomly cross-linked groups:

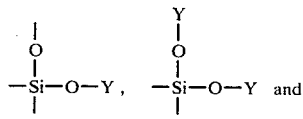

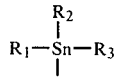

where each Y is independently a trisubstituted tin radical having the formula:

where $R_1$, $R_2$, and $R_3$ are independently selected from the group consisting of alkyl and cycloalkyl radicals, and $R_1$, $R_2$, and $R_3$ contain in combination from 3 to about 18 carbon atoms, where the ratio of tin atoms to silicon atoms in the polysiloxane is from about 1:50 to about 2:5; and where each branch of the polysiloxane independently terminates with a structure selected from the group consisting of hydrogen and alkyl and alkoxyalkyl radicals containing less than about 6 carbon atoms and Y; the method comprising the steps of:

(a) forming droplets of a siloxane having the formula:

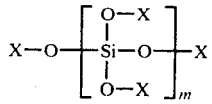

where m is from about 1 to about 10,
where each X is independently selected from the group consisting of alkyl and alkoxyalkyl radicals containing less than 6 carbon atoms and y, and
where the X's are selected so that the ratio of tin atoms to silicon atoms in the siloxane is from about 1:50 to about 2:5, wherein the siloxane is at least partially hydrolyzed; and (b) exposing said droplets to a source of moisture at a temperature sufficient to effect condensation of the siloxane.

2. A method as recited in claim 1 where m is an average of about 5.

* * * * *